United States Patent [19]

Buchanan

[11] Patent Number: 4,737,413
[45] Date of Patent: Apr. 12, 1988

[54] CHEMOREPELLANT COMPOUND

[75] Inventor: Michael R. Buchanan, Toronto, Canada

[73] Assignee: Canadian Patents and Development Limited, Ottawa, Canada

[21] Appl. No.: 880,374

[22] Filed: Jun. 30, 1986

[30] Foreign Application Priority Data

Jul. 11, 1985 [CA] Canada .................................. 486737

[51] Int. Cl.[4] .......................... A01N 1/02; B32B 9/04; C11C 3/02; C12P 7/64
[52] U.S. Cl. .......................... 428/411.1; 260/410.9 R; 260/413; 427/2; 435/134
[58] Field of Search .................. 260/410.9 R, 413; 427/2; 435/134; 428/411.1

[56] References Cited

PUBLICATIONS

W. H. Tallent et al., "(R)-13-hydro-xy-cis-9, trans-1-1-octadeca dienoie acid, the Principal Fatty Acid from *Coriaria napaleusis* Seed Oil", Nov. 21, 1966, Chemical Abstracts, vol. 65, No. 11.

M. O. Funk et al., "The Preparation and Characterization of the Methoxy Derivatives of Polyunsaturated Fatty Acids; Stabilized Product Analogs of Lipoxygenase Catalysis", May 11, 1981, Chemical Abstracts, vol. 94, No. 19.

K. L. Mikolajczak et al., "Effect of Oat Constituents on Aggregation Behavior of Oryzaephilus Surinamensis", Jan. 31, 1983, Chemical Abstracts, vol. 98, No. 5.

Primary Examiner—Michael R. Lusignan
Attorney, Agent, or Firm—Rogers & Scott

[57] ABSTRACT

A chemorepellant compound is disclosed having a general formula

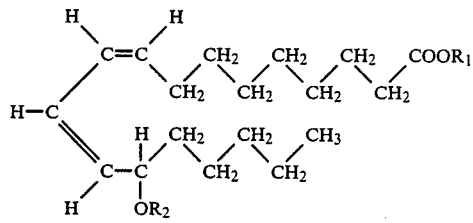

where $R_1$ is H or an alkyl group in the range $C_1$ to $C_6$, and $R_2$ is H or an appropriate hydroxyl protecting group, and pharmaceutically acceptable salts and esters thereof. A preferred form of the compound where $R_1$ is hydrogen and $R_2$ is hydrogen is made by incubating linoleic acid with soyabean lipoxygenase or with cytosol associated endothelial cell derived lipoxygenase. The chemorepellant compound can be bound to a prosthetic surface via an intermediate linking species such as a protein and studies have shown that platelet adhesion onto in the vicinity of a thrombogenic surface is greatly reduced in comparison to non-chemorepellant coated surfaces.

12 Claims, 6 Drawing Sheets

STANDARDS
—— MEDIA
----- 13-HODE
—·— 15-HETE
—··— 12-HETE

RETENTION TIME (MINUTES)

ABSORBANCE (236 nm)

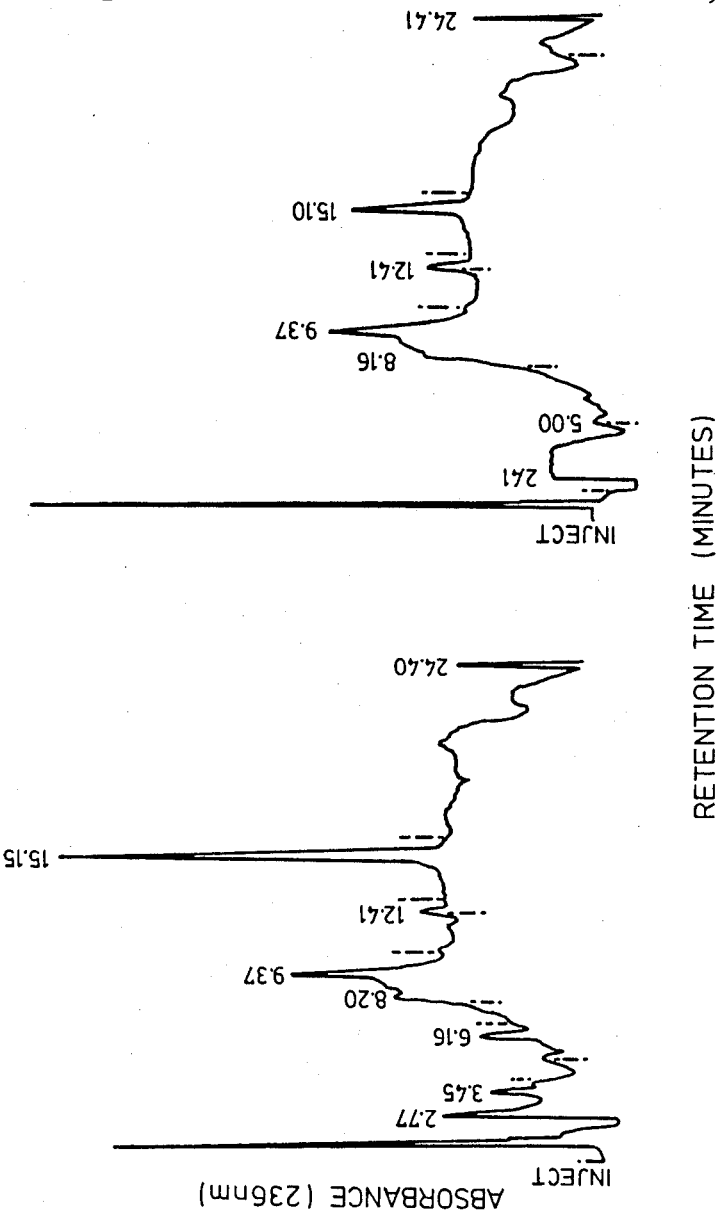

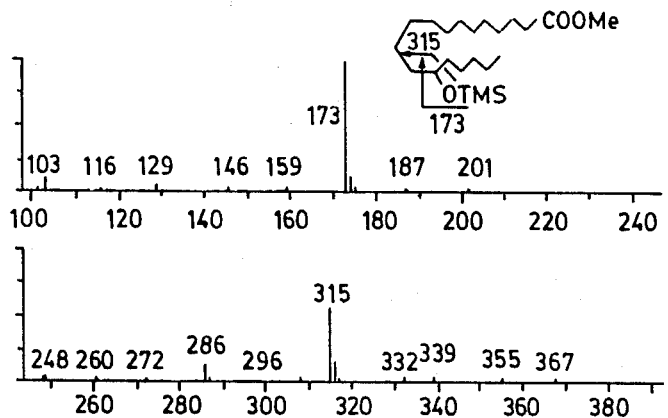
FIG. 4a GC/MS PROFILE OF PURIFIED HYDROGENATED 13-HODE
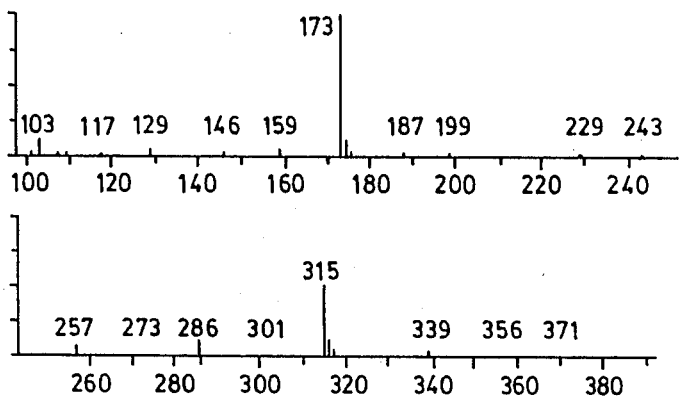
FIG. 4b GC/MS PROFILE OF ENDOTHELIAL CELL LIPOXYGENASE EXTRACT, 15 MIN. PEAK
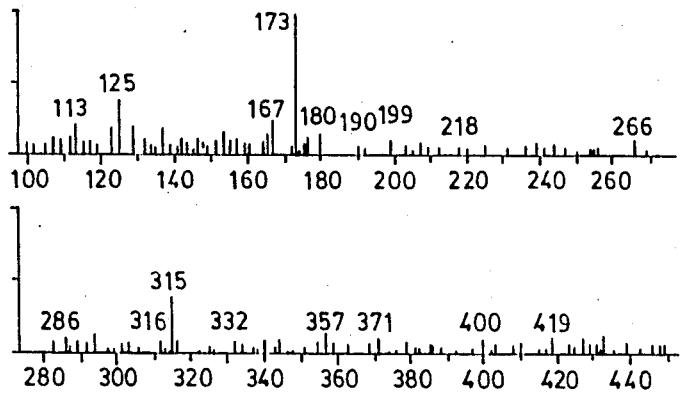
FIG. 4c GC/MS PROFILE OF SMOOTH MUSCLE EXTRACT 15 MIN. PEAK

CHEMOREPELLANT COMPOUND

The present invention relates to a chemorepellant compound for attachment to a prosthetic surface for use in human and animal cardiovascular systems to provide a biocompatible surface with reduced thrombogenecity. In particular, the invention also relates to a method of manufacturing the chemorepellant compound, to a method of attaching the compound to a prosthetic surface and to a method or use of the compound in vivo.

For many years, numerous investigators have tried to develop a suitable biocompatible surface for prosthetic materials when used as a replacement material within the cardiovascular system. This has been difficult to achieve because a wide variety of prosthetic substances are necessary such as, flexible polymers and rigid meterials since these materials are selected not only for their desirable surface characteristics but also for their physical properties. However, no artificial surface currently available is wholly compatable with blood and despite considerable research no artificial surface has been found which is as inert towards blood as the endothelial surface of blood vessels. In particular, all artificial surfaces tend, to some extend, to activate blood coagulation, and to attract platelets and leukocytes, although some materials appear to be less reactive than others. Some specific undesirable properties of biomaterials have been identified. For example, it has been found that highly charged surfaces or surfaces with a rough texture are reactive and should be avoided. It has been found that very smooth prosthetic surfaces are desirable because it appears that surface irregularities may enhance thrombus formation, probably by producing local disturbances and flow that favour cell adhesion and promote fibrin formation. Irregular surfaces may also be prone to retention of small air bubbles that can serve as nidus for thrombus formation.

The use of prosthetic surfaces that contact blood produces a highly complex situation with respect to the blood components. This situation is brought about by surface contact and alteration of certain plasma proteins as well as by adhesional blood cells. In addition, the mechanical effects of elevated shear stress can alter plasma proteins in blood cells in undesirable ways. For example, blood pumps and heart valves can mechanically damage cells and denature plasma proteins. Consequently, blood anticoagulants have been used in renal dialysis, prosthetic heart valve implantation, extracorporeal oxygenation and blood detoxification by extracorporeal sorption devices.

Exposure of blood to artificial surfaces can lead to several different consequences, the principal ones of which are thrombosis and embolization. Thrombosis occurs when clots develop on an artificial surface and impede the function of the artificial organ such as a prosthetic heart valve or vascular graft. To a certain extent the haemodynamic effects dictate the nature of thrombus formation. For example, in areas of slow blood flow such as the reservoir of pump-oxygenator a red fibrin clot may develop whereas in the regions of high fluid shear rates, such as an arterial bypass graft platelet accumulation may be more prominent. Embolization is the event when a thrombus formed in one site of the cardio vasular is swept downstream to resituate in a vessel or organ. For example, in cerebral embolization a thrombus formed on a prosthetic heart valve may embolize and cause a cause of strokes. Clearly, this is a very serious situation and as such thrombus formation and subsequent embolization can result in serious injury and even death.

It is therefore very desirable that a prosthetic surface should minimize thrombogenecity and subsequent embolization of thrombus formation. In this regard, it is important that the prosthetic surface attempt to simulate the biocompatibility of the endothelium or the luminal lining of healthy blood vessels which do not promote blood clotting or the adharance of circulatory blood cells under normal circumstances. However, it will be appreciated that following injury the endothelial surface becomes the site of a complex reparative reaction following coagulation, fibrmolysis and platelet and leukocyte and blood-cell vessel wall interactions.

At present, there is no artificial substance which is comparable to the endothelium and freed of thrombotic effects. Studies have indicated that there may be an active role for products of endothelial metabolism in inhibiting platelet activity at the vessel wall. In this regard, some investigators have attached biologically active molecules to solid materials in an effort to produce "actively" antithrombogenic materials. For example, heparin coated prosthetic surfaces have been widely used. However subsequent studies have shown that heparin will leach from the surface and generally form a film of anticoagulative blood at the interface which is responsible for reduced thrombus formation rather than from any intrinsic properties of the surface itself. Clinically heparinized prosthetic surfaces have had mixed success and continues to be a problem in understanding how heparin coated surfaces affect the thromboresistance. In fact, heparin has been shown to induce platelet aggregation and enhance platelet responses to other stimuli under some circumstances.

Other materials have been used to coat prosthetic surfaces prior to contacting with blood and there have been claims for reduced reactivity with platelets. For example, covalently bound albumin has been used to coat artificial materials and although some early results were encouraging long term thromboresistance has not been obtained. More active inhibitors of platelet adhesion such as postaglandin and aspirin have also been attached to some polymers, however, results have been inconsistent and long-term assessment of in-vitro or in-vivo thromboresistance has not been reported.

It should be understood that for successful function of prosthetic surfaces in the cardiovascular system total freedom from thrombosis is not essential. For example, an arterial prosthesis made from knitted dacron invariably accumulates an inner layer of fibrin-platelet thrombus and is gradually invaded by fibroblasts and capillary buds and then coated by a layer neoendothelium. However, the graft functions well to transport blood provided its diameter is sufficiently large to obviate occlusion of the lining by thrombus formation. The same criteria applies to the rigid frame of prosthetic heart valves which can also tolerate a thin layer of adherent thrombus. However, it should also be appreciated that the success of such devices is contingent on the fact that the thrombus does not form or impinge on moving components or break off form emboli and subsequently block vessels. For this reason fibrin-coated surfaces have been used to insure against detachment of the thrombotic coat. It has been found that endothelium will grow from the host vessel over the interior of such a device to provide an endothelial layer facing the blood to stabilize the situation. It will be appreciated however that results with such systems are uncertain and it is very desirable to provide a prosthetic surface which is as inert as possible to blood and which minimizes thrombogenecity which would greatly assist in the preventing of clotting and subsequent embolization from detatched clots.

It is an object of the present invention to provide an anti-thrombogenic or chemorepellant compound for attachment to a prosthetic surface for location in the cardiovascular system to provide improved biocompatability on the surface over existing biocompatible materials.

It is also an object of the invention to provide a method of manufacturing such a chemorepellant compound and for providing a method of use of the compound.

Accordingly, there is provided a chemorepellant compound having the formula

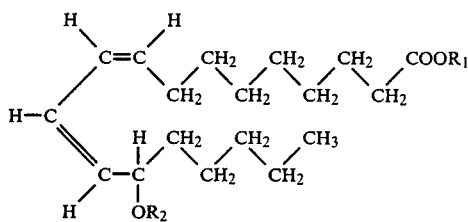

where $R_1$ is H or an alkyl group in the range $C_1$ to $C_6$, and $R_2$ is H or an appropriate hydroxyl protecting group, and pharmaceutically acceptable salts and esters thereof.

According to another aspect of the invention there is provided a method of manufacturing a chemorepellant compound having the structural formula

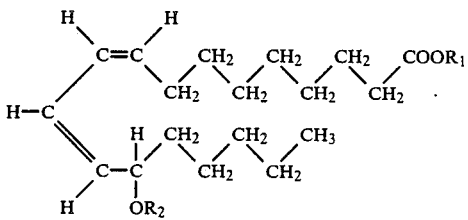

where $R_1$ is H or an alkyl group in the range $C_1$ to $C_6$, and $R_2$ is H or an appropriate hydroxyl protecting group, and pharmaceutically acceptable salts and esters thereof, said method comprising the steps of providing a supply of endothelial cells, incubating said supply of endothelial cells with linoleic acid in a media for a predetermined incubation period or with cytosol assocaited endothelial cell derived lipoxygenase.

According to yet another aspect of the present invention there is provided a method of rendering a prosthetic surface thromboresistant comprising the steps of:

coating said prosthetic surface with a chemorepellant binding species to form a coated prosthetic surface then further coating said coated prosthetic surface with a chemorepellant compound having the formula

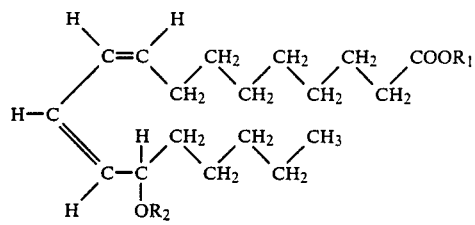

where $R_1$ is H or an alkyl group in the range $C_1$ to $C_6$, and $R_2$ is H or an appropriate hydroxyl protecting group, and pharmaceutically acceptable salts and esters thereof to provide a thromboresistant prosthetic surface.

According to yet another aspect of the present invention there is provided a thromboresistant surface for use in a vascular system, consisting of a prosthetic material, an intermediate species linked to said prosthetic material and a chemorepellant compound having the formula

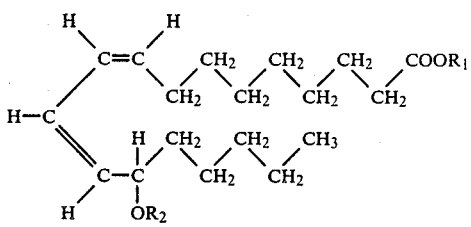

where $R_1$ is H or an alkyl group in the range $C_1$ to $C_6$, and $R_2$ is H or an appropriate hydroxyl protecting group, and pharmaceutically acceptable salts amd esters thereof in a pharmaceutically effective amount attached to said intermediate species, said chemorepellant compound forming an outer surface for contacting blood.

According to yet further aspect of the invention there is provided a thromboresistant surface for use in a vascular system, said thromboresistant surface having a prosthetic base material, a protein linked to said base material to provide a binding substrate, and a chemorepellant compound having the formula L-13 hydroxy-cis-9, trans-11 octadecadienoic acid, and the structure:

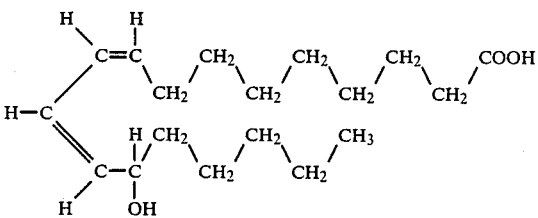

said chemorepellant compound being linked to said binding substrate and providing a blood-contactable thromboresistant surface.

In a preferred embodiment of the invention the chemorepellant compound has formula 13 - OH - 18:2 and the structural formula L-13 hydroxy-cis-9, trans-11 octadecadienoic acid, and the structure:

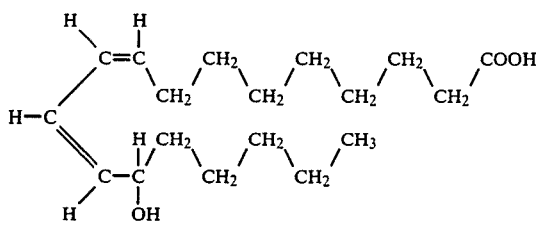

Preferably the compound is made by reacting endothelial cells with linoleic acid for a predetermined period and producing significant production of metabolite cells of the order of 1nM/10[6] cells of culture and in a preferred method of using the compound albumin is coated onto a prosthetic surface and the albumin coated surface is reacted with a pharmaceutically effective concentration of the chemorepellant compound which adheres to the albumin to provide a thromboresistant coating.

A preferred chemorepellant compound has the formula L-13 hydroxy-cis-9, trans-11 octadecadienoic acid, and the structure:

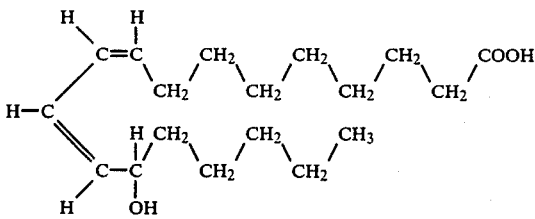

is used and is attached to a prosthetic surface via an intermediate binding agent which is a protein.

These and other aspects of the invention will become apparent from the following description when taken in combination with the accompanying drawings in which.

FIGS. 3a-d show reverse phase high performance liquid chromatography (HPLC) tracings of (a) standards, media, 12-HETE, 15-HETE and the chemorepellant compound (13-HODE); (b) endothelial cell extract; (c) smooth muscle extract; and fibroblast extract; and FIGS. 4a-C are Gas Chromatography/Mass Spectroscopy (GC/MS) output profiles of a reduced form of purified hydrogenerated chemorepellant compound (13-HODE).

Figure 5:
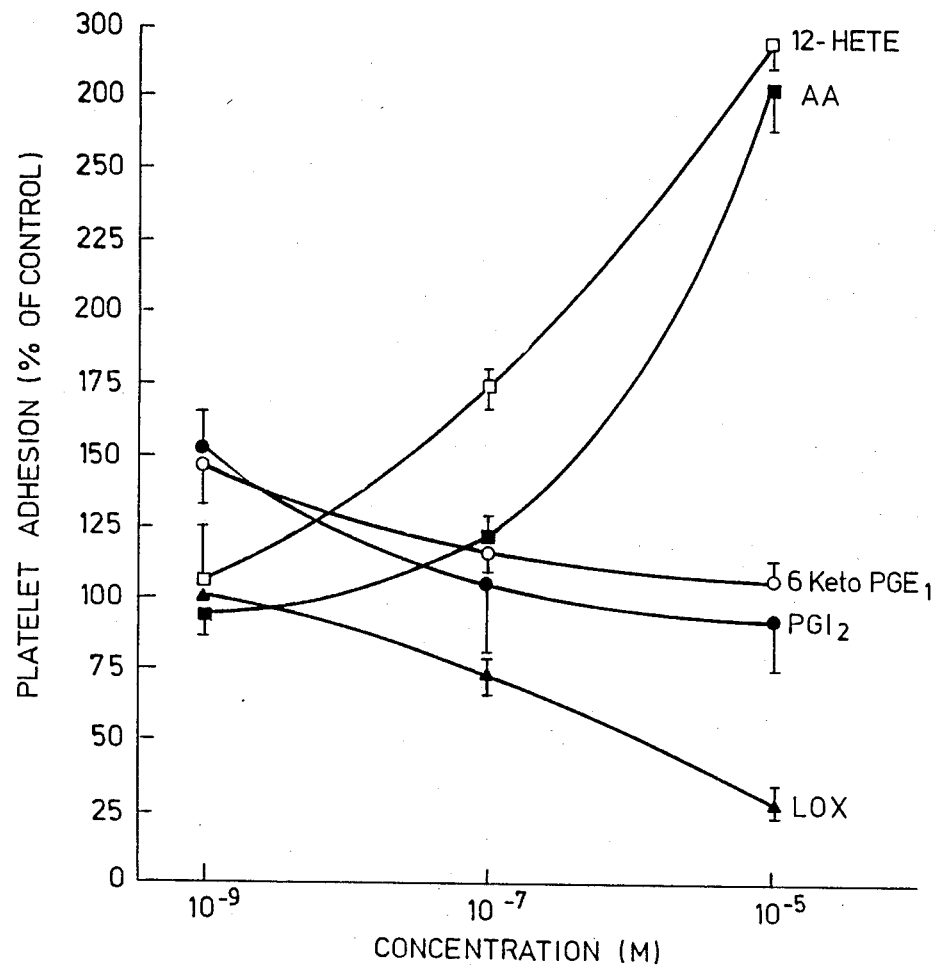
Figure 6:
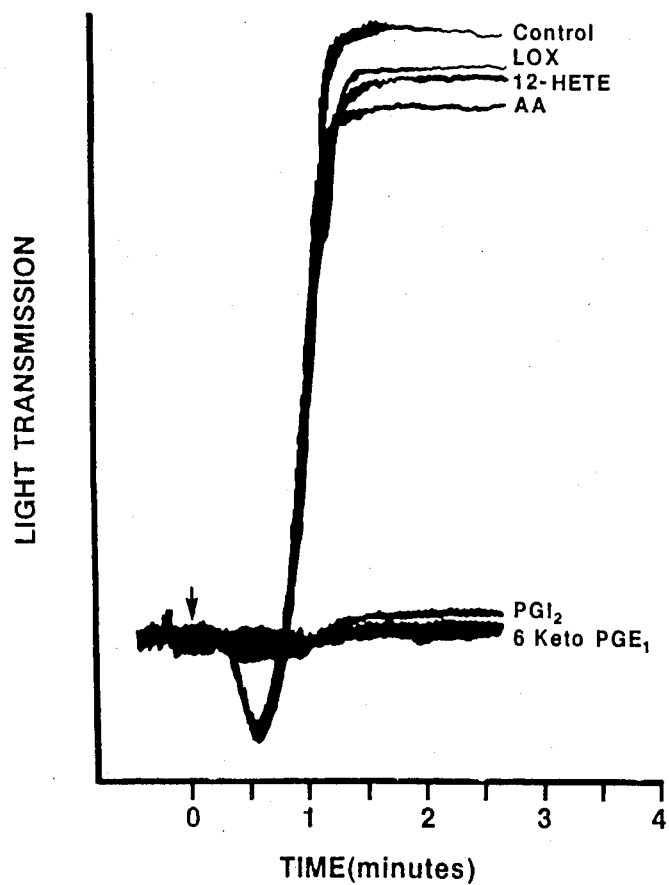

FIG. 5 is a graph illustrating the platelet adhesion (as a percentage of control), versus the concentration of 12-HETE, LOX PGI$_2$, and 6-keto PGE$_1$ to Thermonox ® plastic discs; and FIG. 6 is a graph of light transmission versus time for determining the collagen induced platelet, aggregation of platelets exposed to but not adherent in discs incubated in LOX. 12-HETE, arachidonic acid (AA, PGI$_2$ or 6-keto PGE$_1$) in which the arrow indicates the addition of collagen at time zero.

The following description discloses the materials and methods for the manufacture of the preferred compound; the subsequent analysis and confirmation of the structure, and a method of binding the chemorepellant compound to a prosthetic surface.

Figure 1:
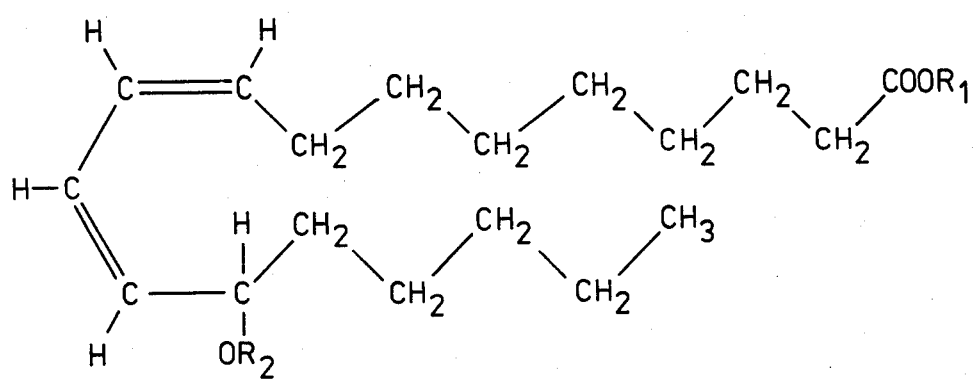
FIG. 1 is a general structural formula of the chemorepellant compound.
Figure 2:
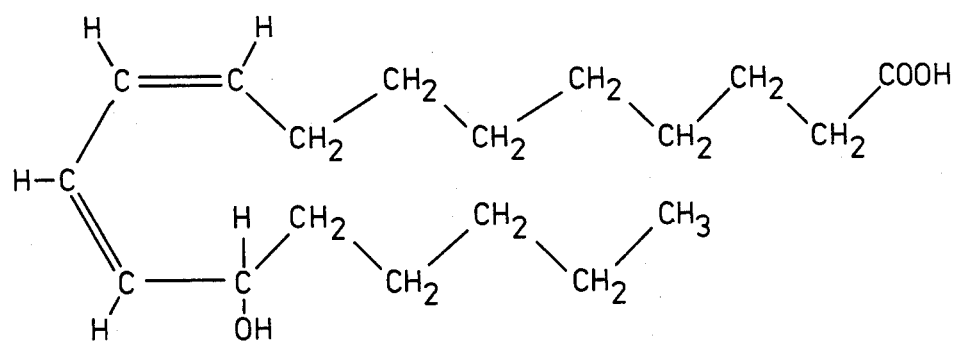
FIG. 2 is a preferred structural formula of the chemorepellant compound according to a preferred method of manufacturing said chemorepellant compound.

The general formula includes a ring structure with double bonds; cis-cis 9-12 octadecadienoic acid having modified by the enzyme to 9-cis 11-trans octadecadienoic acid as shown in FIG. 2 with the OH group attached at C-13. However the Hydrogen on the carboxyl group and on the hydroxyl group can be substituted, as later described, to provide pharmaceutically acceptable salts and esters thereof, as given by the general structural formula shown in FIG. 1. The hydroperoxide bond is generally believed to be unstable in fatty acids or acid metabolites and is believed to be the reason for the chemorepellant properties.

Materials and Methods

U-$^{14}$C-inoleic acid ([14]C-18:2) and U-[14]Carachidonic acid ([14]C-20:4) were obtained for New England Nuclear, Boston, Mass. Soybean lipoxygenase (EC.1.12.11.12), linoleic acid (18:2), arachidonic acid (20:4) and calcium ionophore (A23187) were obtained from Sigma Corp., St. Louis, Mo. All cell culture materials were obtained from GIBCO, Grand Island, N.Y. Pooled human sera were obtained from the Canadian Red Cross, Hamilton, ONT. The sera were heat-inactivated at 56° C. for 30 minutes. All culture glassware was obtained from Costar, Cambridge, Mass.

All solvents and chemicals used for this layer chromatography (TLC), reverse phase high pressure liquid chromatography (HPLC) and gas chromatography/mass spectrometry (GC/MS), were obtained from Fisher Scientific Co., Toronto, ONT., and Interchim, Montlucon, France. TLC was performed usiing silica H plates (20×20cm×250μm) obtained from Supelco, Bellefonte, Pa., and Merck, Darmstadt, FRG. All glassware used for sample preparations were silanized with 4% dimethyldichlorosilane in toluene before use.

HPLC was performed on a NOVA-PAK C$_{18}$ cartridge (5 mm×10 cm) compressed in a RCM-100 column. The M720 Systems Controller allowed for a two-solvent gradient elution (using M45 and a M6000A pumps) and fully automated sample injector (WISP TM). Sample detection was performed on a variable (M480) wavelength absorbance detector at 236 nm, and recorded on a 730 Data Module. All HPLC instruments were obtained from Waters Scientific, Mississauga, ONT.

GC/MS was performed on a SE-54 wall-coated capillary column (22 mm×50 m) which was interfaced in a Nermag quadripolar instrument, (Paris, France).

Cell Culture Preparations

Human umbilical vein-derived endothelial cells were cultured in vitro according to the method of Gimbrone, M.A., Shefton, E.S., and Cruise, S.A. (1978) TCA Manual 4, 813-817), with the following modifications. The cells were grown in M199 supplemented with 20% pooled human heat-inactivated sera (instead of fetal-calf serum), 100 U/ml penicillin, 100 ug/ml streptomycin, 100 ug/ml endothelial cell growth supplement, as disclosed by Maciag, T., Cerundolo, J., Ilsley, S., Kelley, P. R., and Forand, R. (1979) Proc. Natl. Acad. Sci. U.S.A. 76, 5674-5679, and grown on fibronectin-coated T25 flasks. Rat arterial smooth muscle cells (WHK-normotensive rats) were obtained from the Dept. of Anaesthesia, McMaster University and human lung fibroblasts were obtained from the Dept. of Pathology, McMaster University.

HPLC Analysis

Endothelial cell, smooth muscle cells and fibroblasts, and their related medias, were extracted for any lipoxygenase metabolites according to the method of Borgeat, P., de Laclos, B. F., Rabinovitch, H., Picard, S., Braguet, P., Hebert, J., and Lavioette, M. (1984) J. Allergy Clin. Immunol. 74, 310–315). Briefly, the cell medias were transferred to separate tubes containing an equivolume of ice-cold metanol. Then 2 ml of ice-cold methanol (75%) were added to the remaining cells which were then scraped from the T25 flask with a rubber policeman. The particulate fraction was separated from the methanol by centrifugation at 1200 g for 30 minutes at $-10°$ C. The free fatty acids in the methanol supernatant were then assayed by injecting five hundred $\mu$l of the fluid onto a Nova-Pak $C_{18}$ cartridge and eluted off at a flow rate of 1.5 ml/min under 650 PSI using an acetonitrile gradient. It was qualified by measuring its absorbance at 236 nm.

12-HETE, 13-HODE, 15-HETE, 20:4 and 18:2 standards are described as follows:

20:4 and 18:2 were purified by HPLC. 13-OH-9cis, 11-trans-octadecadienoic acid (13-HODE) and 15-hydroxyeicosatetraenoic acid (15-HETE) were prepared by incubating 18:2 and 20:4, respectively, with soybean lipoxygenase according to the method of Hamberg and Samuelsson; Hamberg, M. C., and Samuelsson, B. (1967) J. Biol. Chem. 242, 5329–5335). Platelet-derived 12-hydroxy-eicosatetraenoic acid (12-HETE) was prepared from 20:4 according to the method of Sun, F.F. (1981) Methods of Enzymology 72, 435–442. All metabolites were purified by HPLC.

Samples of cellular or media extracts were further purified for GC/MS analysis by HPLC or alternatively, the monohydroxy derivatives were purified by thin-layer chromatography according to standard methods, disclosed by Croset, M., and Lagarde, M. (1983) Biochem. Biophys. Res. Commun. 112, 878–8830, and then derivatized for GC/MS. Briefly, the lipid extracts were transformed into methylesters by treatment with an ether saturated solution of diazomethane for 15 minutes at 22° C, and then transformed into trimethylsilylethers by N,0-bix0trimethylsilyl-fluoro-acetamide treatment for 1 hour at 40° C. The derivatized extracts were then either hydrogenated or deuterated in the presence of platinum. The derivatized extracts were then injected onto the GC column used with a temperature gradient (170-285° C., 2° /min). The MS conditions for analysis were: electron voltage, 70 eV, electron multiplier, 2 kV.

Experimental Design

Endothelial cells, smooth muscle cells or fibroblasts were incubated in serum free media $\pm 2$ $\mu$M of $^{14}$C-18:2 or $^{14}$C-20:4 for 20 minutes, followed by stimulation for 10 minutes with $\pm$ (unlabelled 18:2 or 20:4) $\pm$ [calcium inonophore (A23187, 1-10 $\mu$M), thrombin (0.1-10 Units/ml) or trypsin (0.0025-0.05%)]. Both the cell extractions and their media were analyzed by HPLC and GC/MS.

Results

Under HPLC, purified 13-HODE, 15-HETE and 12-HETE eluted from the $C_{18}$ column at 14.95–15.15, 15.65–15.80, and 16.85–17.20, minutes respectively as measured at 236 nm (FIG. 3a). When intact and unstimulated endothelial cells were extracted with methanol to obtain the hydroxyl derivatives of the free fatty acids, the major chemorepellant compound (LOX) eluted from the $C_{18}$ column at 14.95-15.15 minutes (FIG. 3b), consistent with 13-HODE. A similar metabolite was also detectable in the extracts from smooth muscle cell (FIG. 3c) and fibroblasts (FIG. 3d), however, the amounts produced by the latter two cell types were significantly less than that produced by endothelial cells.

The structural identity of the chemorepellant compared to the purified 13-HODE was determined by running, the hydroxygenated or deuterated derivatized cell extracts under GC/MS. Endothelial cell LOX, separated by either HPLC or by TLC, exhibited a peak retention time of 35 minutes and co-chromatographed with the hydrogenated form of 13-HODE. As best seen in FIG. 4, their mass spectra were similar with the two main fragments (M/z 173 and 315), corresponding to the breakage on both sides of the OTMS. When the derivatized extracts were subjected to deuteration instead of hydrogenation, the mass spectrum exhibited major fragments at M/z 173 and 319, (data not shown) because of four (4) extra neutrons, indicating that the initial molecule possessed two double bonds between $C_1$ and $C_{12}$. These confirmed that the chemorepellant compound with LOX was 13-OH-18:2. Further GC/MS analysis of the total monohydroxy derivatives indicated that there was no detectable 12-, 15-OH-20:0, 14- or 17-OH-22:0 metabolites. As seen in FIG. 4c, the metabolite produced by smooth muscle cells which also eluted at 15 minutes was also consistent with 13-HODE.

The amount of 13-OH-18:2 produced by unstimulated cells was $3410 \pm 340$ ng/$10^6$ (mean$\pm$SEM) for endothelial cells (n=15). $1650 \pm 350$ ng/$10^6$ for smooth muscle cells (n=5), and $500+70$ ng/$10^6$ for fibroblasts (n=5). When cells were stimulated with thrombin, calcium ionophore (A23187) and trypsin, there were dose-dependent decreases in 13-OH-18:2 were associated with dose-related increases in a 12.5 minute HPLC peak (with A23187), a 9 minute peak (with trypsin), and no new peak with thrombin.

The structural characteristics of the chemorepellant compound shown in FIG. 2, firmly imply that its substrate is 18:2 linoleic acid and by GC/MS it has been confirmed that LOX is structurally compatible with 13-HODE, and is the major lipoxygense metabolite produced by endothelial cells. 13-OH-18:2 was produced in significant amounts by 'unstimulated' endothelial cells and decreased by thrombin, A23187 or trypsin stimulation. The decrease in 13-OH-18:2 with a corresponding increase in other peaks (depending upon the stimulus), suggests that these agents caused either the stimulation of additional metabolites at the expense of 13-OH-18:2 production, or caused some degradation of the cell membrane including 13-OH-18:2, and 13-OH-18:2 was produced by endothelial cells in significantly greater amounts than by either smooth muscle cells or fibroblasts. These observations are consistent with the hypothesis found in a paper by Buchanan, M. R., Butt, R. W., Magas, Z., Van Ryn, J., Hirsh, J. and Nazir, D. J., (July, 1985) Thromb. Haimostas. In Press, which postulated that LOX (13-OH-18:2) acts as an important thromboresistant or 'chemorepellant' factor for the vessel wall under healthy conditions.

No other lipoxygenase-derived metabolites from 20:4 or 22:4 were detected. There are two possible sources of the 18:2 stores necessary for the metabolism of the chemorepellant compound LOX; (i) the phospholipid pools, in particular phosphatidylcholine (PC) and /or phosphatidylinositol (PI), and (ii) the endothelial cells triglyceride pool. The first possibility seems unlikely since the liberation of 18:2 from PC requires the activation of phospholipase $A_2$ described in Jimeno-Abendano, J. and Zahler, P. (1979) Biochim. Biophys. Acta 573, 266–275 which in turn, requires mobilization of calcium described in Jesse R. L. and Franson R. C. (1979) Biochim. Biophys. Acta 575, 467–470. However, 13-OH-18:2 is present in the endothelial cell under basal or unstimulated conditions and at physiological calcium concentrations, two conditions under which phospholipase $A_2$ is not activated. In addition, thrombin, A23187 and trypsin, at concentrations which activate phospholipase $A_2$, did not stimulate 13-OH-18:2 production but rather resulted in a decreased production. Endothelial cell PI is also an unlikely source for 13-OH-18:2 since it is likely to be rich in 20:4 and stearic acid but not 18:2 as in other cells (Marcus, A. J. (1978) J. Lipid Res. 19, 783–826). It is believed that the source for the endothelial cell 18:2 is the triglyceride stores. Denning et al. (J. Lipid Res. 24 (1983) 993–1001) reported that there was a high turnover of fatty acids in the endothelial cell triglyceride pool, and Lagarde et al (In Vitro 20, (1984) 33–37) have reported that a major polyunsaturated fatty acid in endothelial cells triglycerides is 18:2. These two observations are consistent with the hypothesis that 13-OH-18:2 is derived from the substrate, 18:2, stored in triglycerides, and which is continuously produced under basal conditions, as is evidenced by the continuous triglyceride turnover.

Studies of the effectiveness of the chemorepellant compound, prior to its structural details being fully required, by binding the chemorepellant compound to albumin coated plastic discs. Thermanox ® plastic discs were incubated for 18 hours in 1% essentially fatty acid-free Tyrodes albumin at 4° C. The discs were then removed from the albumin suspension, rinsed in a 3-wash series of HBSS and incubated in increasing concentrations of LOX, 12-HETE, arachidonic acid, $PGI_2$ or 6-keto $PGE_1$. Thirty minutes later, each disc was removed and rinsed again in a 3-wash series of HBSS and then incubated in 750 ml. of $^3$H-adenine-labelled platelet suspensions for 30 minutes at 37° C. Adhesion of $^3$H-adenine-labelled platelets to albumin-coated discs was measured using a modification of the platelet/endothelial cell adhesion assay described by Gimbrone, M. A. and Buchanan, M. R., Endothelium, A. P. Fishman (ed). Ann NY Acad Sci 401 (1983), 171–183. In preliminary studies, it was found that 0.8–1.0% $^{14}$C-arachidonic acid, $^3$H-12-HETE and $^3$H-$PGI_2$, regardless of concentrations, ranging from, $10^{-9}$ to $10^{-3}$, bound to the albumin-coated discs. A similar percentage binding charactisteristics for 6-keto-PGF1 and the LOX preparation was assumed.

Platelet adhesion to the fatty acid metabolite-coated discs was then determined as described in the Gimbrone and Buchanan reference mentioned above. Also, at the end of the 30 minute incubation period, the platelets in suspension that were exposed to but not adherent on the fatty acid metabolite-coated discs were tested for collagen-induced platelet aggregation.

Results

Adhesion of aspirin-treated platelets to the Thermanox ® plastic discs coated only with essentially fatty acid-free albumin was 12,140±1,250 platelets/mm$^2$ of disc suface area (100±10%; mean±SEM; n=6, as shown). As seen in FIG. 5, when the albumin-coated discs were incubated for 30 minutes in increasing concentrations of arachidonic acid or 12-HETE, platelet adhesion was significantly increased, p<0.001. In contrast, when the albumin-coated discs were incubated in increasing concentration s of LOX for 30 minutes, platelet adhesion was significantly decreased (p<0.001). Incubating the discs in $PGI_2$ or 6-keto $PGE_1$ had no effect on adhesion.

Collagen-induced aggregation of platelets exposed to but not adherent on the chemorepellant compound-, arachidonic acid-, or 12-HETE-coated discs was unaffected as best seen in FIG. 6, while platelet aggregation was totally inhibited whent he platelets were exposed to the $PGI_2$- or 6-keto $PGE_1$-coated discs.

The observations that the chemorepellant compound inhibited platelet adhesion to the discs but had no effect on platelet aggregation suggests that the effect of chemorepellant compound is a direct effect on platelet adhesion at the disc surface by the chemorepellant compound coating. This is believed to be due to the hydroperoxy group (OH) at site of C-13 which is the active site for chemorepellant activity.

It will be appreciated that the preferred structure shown may be modified by replacing the H of the carboxyl group by the alkyl group having one to six carbon atoms and the H of the OH group may be replaced by an appropriate hydroxy protecting group. It will also be appreciated that pharmaceutically acceptable salts and esters of the compound can be bound to an intermediate binding species such as albumin coated on a prosthetic surface. Also, instead of soyabean lipoxygenase, any other suitable cytosol associated endothelial cell derived lipoxygenase can be used. For example, the Hydrogen of the carboxyl group may be replaced by Sodium, Potassium, Calcium, Magnesium or Aluminum to give pharmaceutically acceptable salts thereof. It is believed that the stereochemical structure has a ring-like structure but it is also likely that a non-ring structure having the same chemical formula is possible.

The embodiments of the invention in which an exclusive property or privilege is claimed are defined as follows:

1. A method of rendering a prosthetic surface thromoresistant, said method comprising attaching to said surface a chemorepellant compound having the formula

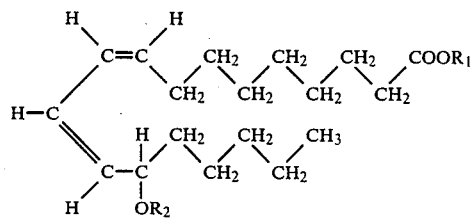

where $R_1$ is H or an alkyl group in the range $C_1$ to $C_6$, and $R_2$ is H or an appropriate hydroxyl protecting group, and pharmaceutically acceptable salts and esters thereof via an intermediate linking species attached to the surface.

2. A method as claimed in claim 1 wherein said intermediate linking species is a protein.

3. A method as claimed in claim 2 wherein said protein is albumin.

4. A method as claimed in claim 1, wherein said chemorepellant compound is attached to said surface in a pharmaceutically effective concentration to minimise thrombosis formation adjacent to said surface.

5. A method as claimed in claim 2 including incubating said albumin coated artificial surface within a pharmaceutically effective concentration of said chemorepellant compound for a predetermined period to provide a pharmaceutically effective concentration on said surface.

6. A method of rendering a prosthetic surface thromboresistant comprising the steps of:
coating said prosthetic surface with a chemorepellant binding species to form a coated prosthetic surface then further coating said coated prosthetic surface with a chemorepellant compound having the formula

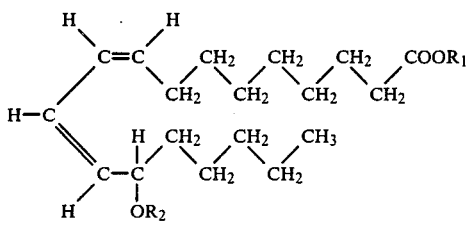

where $R_1$ is H or an alkyl group in the range $C_1$ to $C_6$, and $R_2$ is H or an appropriate hydroxyl protecting group, and pharmaceutically acceptable salts and esters thereof to provide a thromboresistant prosthetic surface.

7. A method as claimed in claim 6 wherein said prosthetic surface is coated with said chemorepellant binding species by incubating said prosthetic surface in a chemorepellant binding species suspension for a first predetermined period, and then further coating said coated prosthetic surface by incubating said coated surface in a suspension of said chemorepellant compound for a second predetermined period.

8. A thromboresistant surface for use in a vascular system, consisting of a prosthetic material, an intermediate species linked to said prosthetic material and a chemorepellant compound having the formula

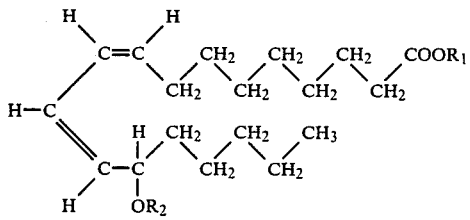

where $R_1$ is H or an alkyl group in the range $C_1$ to $C_6$, and $R_2$ is H or an appropriate hydroxyl protecting group, and pharmaceutically acceptable salts and esters thereof in a pharmaceutically effective amount attached to said intermediate species, said chemorepellant compound forming an outer prosthetic surface for contacting blood.

9. A thromboresistant surface as claimed in claim 8 wherein said intermediate species is a protein.

10. A thromboresistant surface as claimed in claim 9 wherein said protein is albumin.

11. A thromboresistant surface for use in a vascular system, said thromboresistant surface having a prosthetic base material, a protein linked to said base material to provide a binding substrate, and a chemorepellant compound having the formula L-13 hydroxy-cis-9, trans-11 octadecadrenoic acid, and the structure:

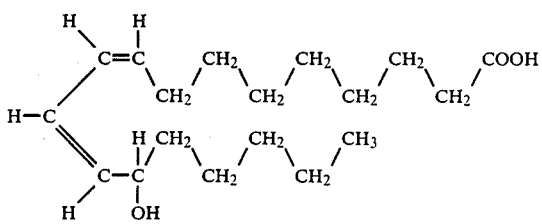

linked to said binding substrate and providing a blood-contactable thromboresistant surface.

12. A method of making a thromboresistant surface for a blood contactable prosthesis comprising the steps of:
providing a prosthetic substrate,
attaching to said prosthetic substrate a chemorepellant binding species to provide a coated surface, and attaching a chemorepellant compound in a pharmaceutically effective amount to said coated substrate to provide said thromboresistant surface, said chemorepellant compound having the formula

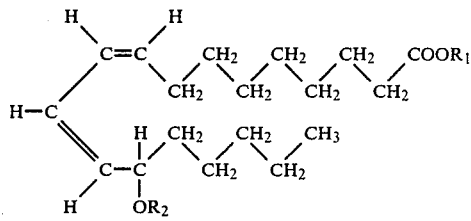

where $R_1$ is H or an alkyl group in the range $C_1$ to $C_6$, and $R_2$ is H or an appropriate hydroxyl protecting group, and pharmaceutically acceptable salts and esters thereof.

* * * * *